US00PP16948P2

(12) United States Plant Patent
Herdegen

(10) Patent No.: US PP16,948 P2
(45) Date of Patent: Aug. 8, 2006

(54) ***EUPHORBIA* PLANT NAMED 'IMPRKALIP'**

(50) Latin Name: *Euphorbia hybrida*
Varietal Denomination: Imprkalip

(75) Inventor: Susanne Herdegen, Dexheim (DE)

(73) Assignee: Innovaplant GmbH & Co. KG, Gensinger (DE)

( * ) Notice: Subject to any disclaimer, the term of this patent is extended or adjusted under 35 U.S.C. 154(b) by 10 days.

(21) Appl. No.: 11/113,388

(22) Filed: Apr. 23, 2005

(51) Int. Cl.
*A01H 5/00* (2006.01)

(52) U.S. Cl. ..... Plt./302

(58) Field of Classification Search ..... Plt./302, Plt./226

See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Euphorbia* plant named 'Imprkalip', characterized by its compact, upright and mounded plant habit; very freely branching habit; and good garden performance.

1 Drawing Sheet

Botanical designation: *Euphorbia hybrida.*
Cultivar denomination: 'Imprkalip'.

BACKGROUND OF THE INVENTION

The present Invention relates to a new and distinct cultivar of *Euphorbia* plant, botanically known as *Euphorbia hybrida*, and hereinafter referred to by the cultivar name Imprkalip.

The new *Euphorbia* is a naturally-occurring whole plant mutation of the *Euphorbia hybrida* cultivar Kalipso, not patented. The new *Euphorbia* was discovered and selected as a single plant from within a population of plants of 'Kalipso' in a controlled environment in Gensingen, Germany in the spring of 2002.

Asexual reproduction of the new cultivar by terminal vegetative cuttings since May, 2002 in Gensingen, Germany has shown that the unique features of this new *Euphorbia* are stable and reproduced true to type in successive generations.

SUMMARY OF THE INVENTION

Plants of the cultivar Imprkalip have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Imprkalip'. These characteristics in combination distinguish 'Imprkalip' as a new and distinct cultivar:

1. Compact, upright and mounded plant habit.
2. Very freely branching habit.
3. Good garden performance.

In side-by-side comparisons conducted in Gensingen, Germany, plants of the new *Euphorbia* differ primarily from plants of the parent, the cultivar Kalipso, in plant growth habit as plants of the new *Euphorbia* are more compact and not as vigorous as plants of the cultivar Kalipso.

Plants of the new *Euphorbia* can be compared to plants of the *Euphorbia* cultivar Humpty Dumpty, not patented. In side-by-side comparisons conducted in Gensingen, Germany, plants of the new *Euphorbia* differed from plants of the cultivar Humpty Dumpty in the following characteristics:

1. Plants of the new *Euphorbia* were more compact than plants of the cultivar Humpty Dumpty.
2. Plants of the new *Euphorbia* were more freely branching than plants of the cultivar Humpty Dumpty.
3. Plants of the new *Euphorbia* had smaller leaves than plants of the cultivar Humpty Dumpty.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Euphorbia.*

The photograph at the top of the sheet is a close-up view of typical leaves of 'Imprkalip'.

The photograph at that bottom of the sheet comprises a side perspective view of a typical plant of 'Imprkalip' grown in a container.

DETAILED BOTANICAL DESCRIPTION

The aforementioned photographs and following observations and measurements describe plants grown in Bonsall, Calif., in an outdoor nursery during the fall and winter under full sun conditions with day temperatures ranging from 13 to 35° C. and night temperatures ranging from 4 to 19° C. After planting rooted cuttings, plants were grown for about 18 weeks in 12.5-cm containers. Plants were pinched one time. Color references are made to The Royal Horticultural Society Colour Chart, 1995 Edition, except where general terms of ordinary dictionary significance are used.

Botanical classification: *Euphorbia hybrida* cultivar Imprkalip.

Parentage: Naturally-occurring whole plant mutation of the *Euphorbia hybrida* cultivar Kalipso, not patented.

Propagation:

*Type*.—By cuttings.

*Time to initiate roots, summer*.—About 14 days at temperatures of 20° C.

*Time to initiate roots, winter*.—About 18 days at temperatures of 20° C.

*Time to develop roots*.—About 20 days at temperatures of 20° C.

*Root description*.—Fine, white in color.

*Rooting habit*.—Freely branching.

Plant description:

*Plant form and growth habit*.—Compact, upright and mounded plant habit; columnar; perennial subshrub. Slow growth rate.

*Branching habit*.—Very freely branching, usually about 24 lateral branches develop per plant; dense and bushy plant form.

*Plant height*.—About 18 cm.

*Plant diameter*.—About 24 cm.

*Lateral branch description*.—Length: About 14 cm. Diameter: About 5 mm. Internode length: About 6 mm. Strength: Strong. Texture: Pubescent. Color: 145B.

Foliage description:

*Arrangement*.—Alternate to whorled; simple.

*Length*.—About 4.3 cm.

*Width*.—About 9 mm.

*Shape*.—Obovate to elliptical.

*Apex*.—Broadly acute.

*Base*.—Attenuate.

*Margin*.—Entire.

*Texture, upper surface*.—Glabrous; smooth.

*Texture, lower surface*.—Pubescence along the mid-vein and margins.

*Venation*.—Pinnate, arcuate.

*Color*.—Developing foliage, upper and lower surfaces: 146B. Fully developed foliage, upper and lower surfaces: 147A to 147B; towards the apex, tinged with 183B. Venation, upper surface: 146C. Venation, lower surface: 147C.

*Petiole*.—Length: About 7 mm. Diameter: About 2 mm. Texture, upper and lower surfaces: Slightly pubescent. Color, upper and lower surfaces: 146D.

Flower description: Flower development has not been observed on plants of the new *Euphorbia*.

Disease/pest resistance: Plants of the new *Euphorbia* not been observed to be resistant to pathogens and pests common to *Euphorbia*.

Temperature tolerance: Plants of the new *Euphorbia* are tolerant to temperatures as low as −6° C. and as high as 40° C.

It is claimed:

1. A new and distinct *Euphorbia* plant named 'Imprkalip', as illustrated and described.

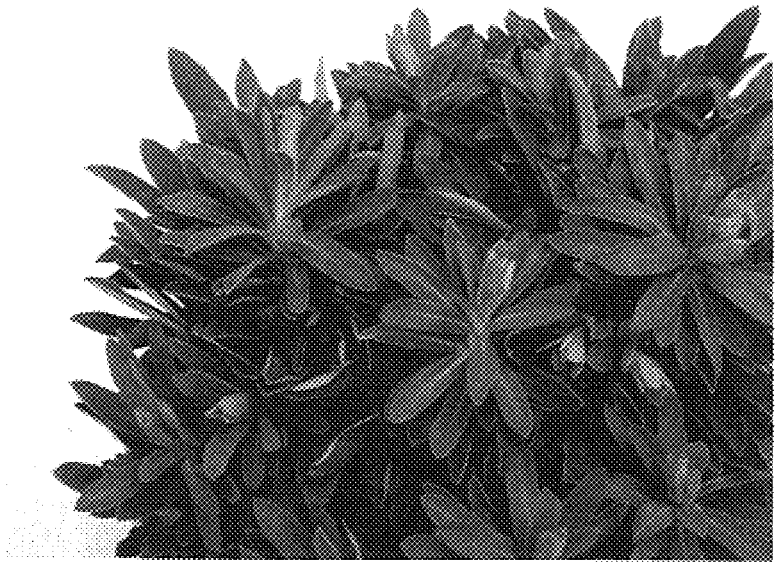
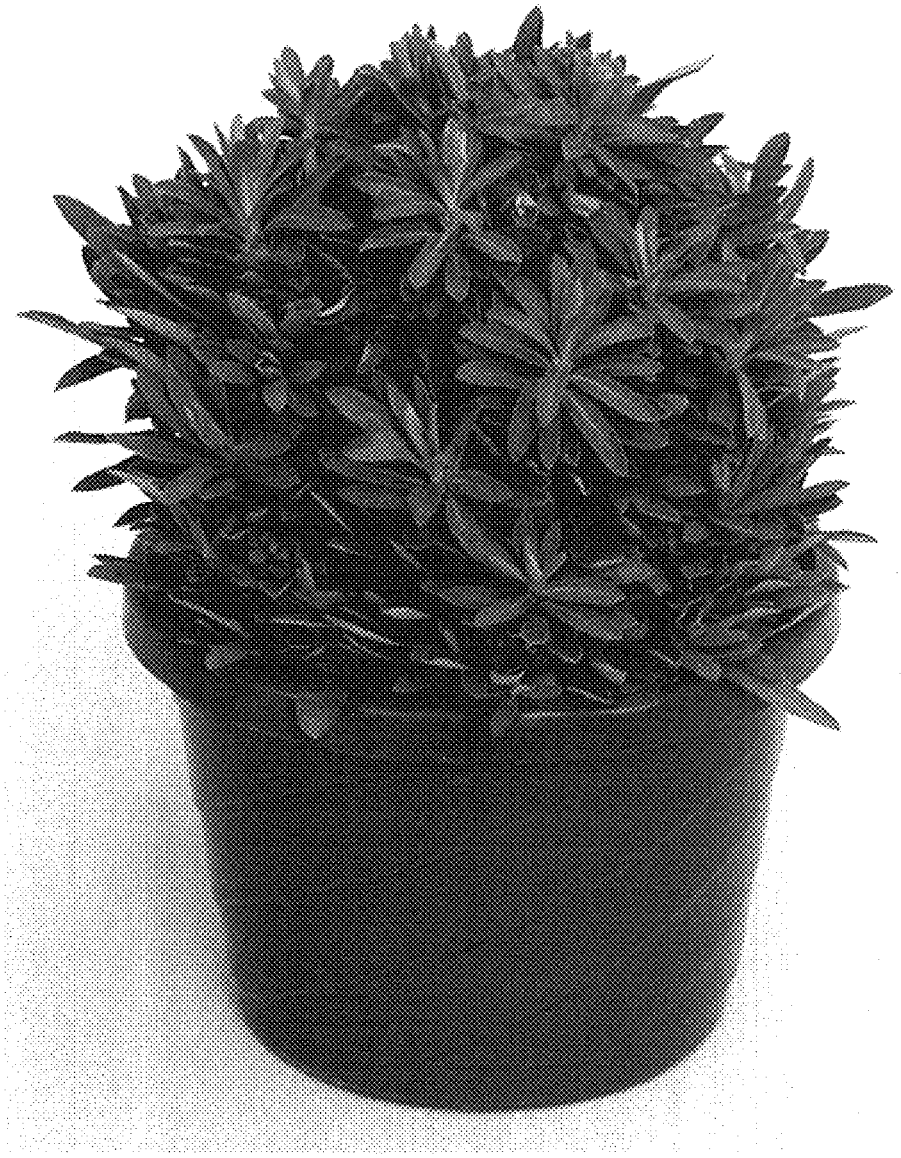

* * * * *